(12) United States Patent
Schmidt et al.

(10) Patent No.: US 12,374,111 B2
(45) Date of Patent: Jul. 29, 2025

(54) EVENT-CONTROLLED VIEW SELECTION

(71) Applicant: KONINKLIJKE PHILIPS N.V., Eindhoven (NL)

(72) Inventors: Joachim Dieter Schmidt, Hamburg (DE); Thomas Erik Amthor, Hamburg (DE); Tanja Nordhoff, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 387 days.

(21) Appl. No.: 18/015,741

(22) PCT Filed: Jul. 1, 2021

(86) PCT No.: PCT/EP2021/068188
§ 371 (c)(1),
(2) Date: Jan. 12, 2023

(87) PCT Pub. No.: WO2022/012954
PCT Pub. Date: Jan. 20, 2022

(65) Prior Publication Data
US 2023/0316751 A1 Oct. 5, 2023

Related U.S. Application Data

(60) Provisional application No. 62/705,738, filed on Jul. 14, 2020.

(51) Int. Cl.
*G06V 20/40* (2022.01)
*A61B 5/00* (2006.01)
*G16H 40/67* (2018.01)

(52) U.S. Cl.
CPC .............. *G06V 20/44* (2022.01); *A61B 5/742* (2013.01); *G16H 40/67* (2018.01)

(58) Field of Classification Search
CPC ........ G06V 20/44; A61B 5/742; G16H 40/67; H04L 67/12
See application file for complete search history.

(56) References Cited

U.S. PATENT DOCUMENTS 3,646,606 A   2/1972  Buxton
7,256,708 B2  8/2007  Rosenfeld
(Continued)

FOREIGN PATENT DOCUMENTS

WO    2019/063567 A1    4/2019

OTHER PUBLICATIONS

International Search Report and Written Opinion Dated Sep. 23, 2021 for International Application No. PCT/EP2021/068188 Filed Jul. 1, 2021.
(Continued)

*Primary Examiner* — Kent Yip

(57) ABSTRACT

A method (100) of controlling a user interface (UI) provided by a remote operator workstation of a remote expert (RE) providing assistance to local operators (LO) of respective medical imaging devices (2) during a medical imaging examination includes: analyzing signal feeds (17, 18, 9) received by a feed aggregator (15) to detect events occurring in workspaces of the local operators; identifying a highest priority event from amongst the detected events using an event prioritization mapping; identifying a highest priority local operator as the local operator in whose workspace the highest priority event occurred; selecting a highest priority UI view corresponding to the highest priority event using the event-to-UI view mapping; and presenting information derived from the signal feeds from the workspace of the highest priority local operator in accordance with the highest priority UI view.

20 Claims, 2 Drawing Sheets

(56) References Cited

U.S. PATENT DOCUMENTS

| | | | |
|---|---|---|---|
| 7,991,625 B2 | 8/2011 | Rosenfeld | |
| 2004/0260790 A1 | 12/2004 | Balloni | |
| 2016/0124619 A1 | 5/2016 | McCallum | |
| 2017/0105701 A1* | 4/2017 | Pelissier | A61B 8/461 |
| 2018/0247024 A1* | 8/2018 | Divine | G16H 40/20 |
| 2020/0279640 A1* | 9/2020 | Amthor | A61B 5/0046 |

OTHER PUBLICATIONS

Hripcsak, et al: "Design of a Clinical Event Monitor", Computers and Biomedical Research 29, 194-221 (1996).

* cited by examiner

EVENT-CONTROLLED VIEW SELECTION

CROSS REFERENCE TO RELATED APPLICATIONS

This application is the U.S. National Phase application under 35 U.S.C. § 371 of International Application No. PCT/EP2021/068188 filed Jul. 1, 2021, which claims the benefit of U.S. Provisional Patent Application No. 62/705,738 filed Jul. 14, 2020. These applications are hereby incorporated by reference herein.

The following relates generally to the imaging arts, remote imaging assistance arts, remote imaging examination monitoring arts, and related arts.

BACKGROUND

Radiology Operations Command Center (ROCC) systems and methods provide remote technologist, remote expert, or "supertech" assistance to a local technologist performing an imaging examination. The remote expert is expected to be concurrently assigned to assist a number of different imaging bays at different sites that may be spread out across different cities or different states. To accommodate this, the remote workstation used by the supertech is expected to provide three standard views: an enterprise view showing the geographic distribution of sites; a site view showing an overview of all scanners being assisted at a given site; and a room view showing an overview of the status of a single imaging bay.

The super-tech has a workstation that receives a shared or scraped copy of the imaging device controller display, and also has access to video feeds of the scanner room (room cam) and possibly also of the imaging examination region (bore cam).

To be commercially viable, it is expected that the super-tech will be assigned to multiple imaging bays at any given time. This is feasible because, even for a complex imaging examination, the local technologist is expected to be well-qualified to perform most of the imaging examination, and will only need super-tech assistance for small portions of the exam. The super-tech workstation provides various views, such as an enterprise view showing a map of the sites of the imaging bays assigned to the super-tech, a site view providing a more detailed summary table of all imaging bays at a given site assigned to the super-tech, for example listing the examination status for each bay, and a room view which shows the controller display and/or video feed(s) from a single imaging bay. The super-tech can switch between views, and particularly can switch to the room view of a specific imaging bay while assisting that bay.

However, this multitasking environment can be taxing for the supertech.

The following discloses certain improvements to overcome these problems and others.

SUMMARY

In one aspect, a system for supporting a remote expert in assisting local operators of respective medical imaging devices during medical imaging examinations includes a feed aggregator operatively connected to receive signal feeds from electronic devices disposed in workspaces of the local operators. A remote workstation provides a user interface (UI) with selectable UI views for presenting information derived from the signal feeds from the workspace of a selected local operator in accordance with a selected UI view. The workstation includes at least one display device and at least one user input device. A non-transitory data storage stores an event prioritization mapping that maps events to priority levels and an event-to-view mapping that maps events to UI views. An electronic processor is programmed to: analyze the signal feeds received by the feed aggregator to detect events occurring in the workspaces of the local operators; identify a highest priority event from amongst the detected events using the event prioritization mapping; identify a highest priority local operator as the local operator in whose workspace the highest priority event occurred; select a highest priority UI view corresponding to the highest priority event using the event-to-UI view mapping; and present information derived from the signal feeds from the workspace of the highest priority local operator in accordance with the highest priority UI view.

In another aspect, a non-transitory computer readable medium stores instructions executable by at least one electronic processor to perform a method of controlling a UI provided by a remote operator workstation of a remote expert providing assistance to local operators of respective medical imaging devices during a medical imaging examination. The method includes: analyzing signal feeds received from workspaces of the local operators to detect events occurring in the workspaces of the local operators; identifying a highest priority event from amongst the detected events using an event prioritization mapping; identifying a highest priority local operator as the local operator in whose workspace the highest priority event occurred; selecting a highest priority UI view corresponding to the highest priority event using an event-to-UI view mapping; and presenting information derived from the signal feeds from the workspace of the highest priority local operator in accordance with the highest priority UI view.

In another aspect, a method of controlling a UI provided by a remote operator workstation of a remote expert providing assistance to local operators of respective medical imaging devices during a medical imaging examination includes: analyzing signal feeds received from workspaces of the local operators to detect events occurring in the workspaces of the local operators; identifying a highest priority event from amongst the detected events using an event prioritization mapping by inputting the signal feeds into a look-up table that associates a priority level to the events in the signal feeds; identifying a highest priority local operator as the local operator in whose workspace the highest priority event occurred; selecting a highest priority UI view corresponding to the highest priority event using an event-to-UI view mapping by inputting the identified highest priority event into a look-up table to select the highest priority UI view; and presenting information derived from the signal feeds from the workspace of the highest priority local operator in accordance with the highest priority UI view.

One advantage resides in providing a remote expert or radiologist assisting a technologist in conducting a medical imaging examination with positional awareness of local imaging examination(s) which facilitates providing effective assistance to one or more local operators at different facilities.

Another advantage resides in automatically providing a situation-contextual view on a computer of a remote expert of a local operator needing assistance.

Another advantage resides in identifying a most urgent event for the attention of a remote expert from a set of events occurring at multiple imaging bays.

Another advantage resides in identifying an appropriate view for a remote expert based on an identified most urgent event from a set of events occurring at multiple imaging bays.

Another advantage resides in improving efficiency of assistance from a remote expert to one or more local operators.

Another advantage resides in providing customized screen layouts on a computer for a remote expert to assist one or more local operators.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

The following discloses an event-controlled view selection for a remote workstation operable by the remote expert. To this end, sensors are installed in each imaging bay that generate event signals. The imaging device controller and possibly other computerized ancillary equipment (e.g., a contrast injector) are also modified to generate software event signals. A signal receiver translates these event signals into digital data that are sent to the remote center server or directly to the super-tech workstation.

At the remote center server and/or super-tech workstation, the events are analyzed. In a first stage, a prioritization is performed-if two or more events from the same or different imaging bays are received at (about) the same time, then the most important event is identified. This can be done, for example, using a data structure (e.g. look-up table) that associates priority levels or scores to events.

The highest priority event is then input to another data structure that identifies the most appropriate workstation view for that event. For example, the most appropriate view will likely be some configuration of a room view of the imaging bay that generated the event. Depending on the type of event, the room view may show a full-screen view of the controller display (for events relating to scan configuration or image review, for example), or a full-screen view of a bore cam imaging the bore of an imaging device (for an event relating to a patient loaded into the bore for imaging, e.g. patient motion or a patient-initiated call signal), a full-screen view of the room cam (e.g. for an issue with patient loading or unloading), or some combination of these. The super-tech workstation is then set to present that most appropriate view.

Figure 1:
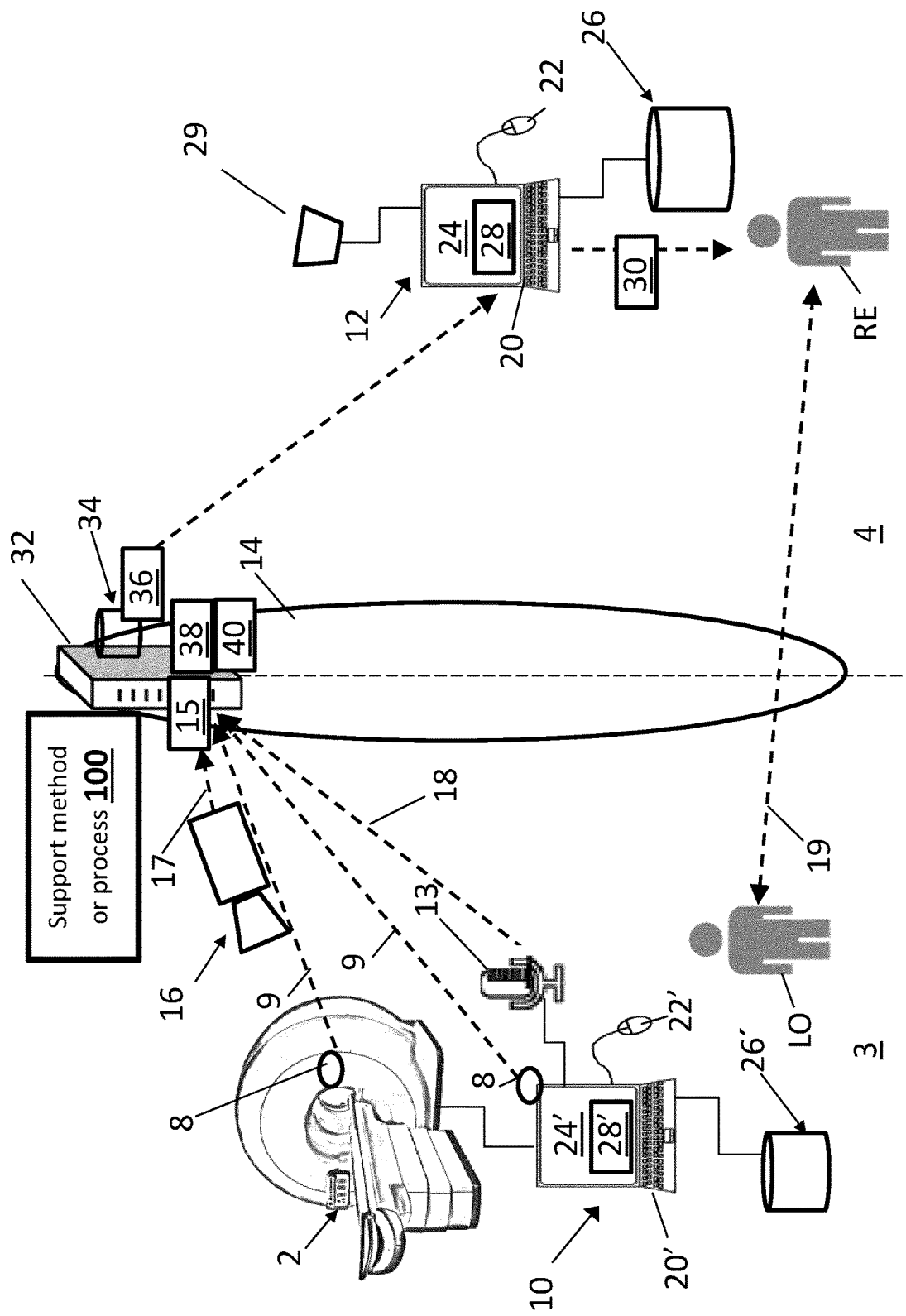
FIG. 1 diagrammatically shows an illustrative apparatus for providing remote assistance in accordance with the present disclosure.

With reference to FIG. 1, an apparatus 1 for providing assistance from a remote medical imaging expert RE (or supertech) to a local technologist operator LO is shown. As shown in FIG. 1, the local operator LO, who operates a medical imaging device (also referred to as an image acquisition device, imaging device, and so forth) 2, is located in a medical imaging device bay 3, and the remote expert RE is disposed in a remote service location or center 4. It should be noted that the "remote expert" RE may not necessarily directly operate the medical imaging device 2, but rather provides assistance to the local operator LO in the form of advice, guidance, instructions, or the like. The remote location 4 can be a remote service center (e.g., a ROCC), a radiologist's office, a radiology department, and so forth. The remote location 4 may be in the same building as the medical imaging device bay 3 (this may, for example, in the case of a "remote operator or expert" RE who is a radiologist tasked with peri-examination image review), but more typically the remote service center 4 and the medical imaging device bay 3 are in different buildings, and indeed may be located in different cities, different countries, and/or different continents. In general, the remote location 4 is remote from the imaging device bay 3 in the sense that the remote expert RE cannot directly visually observe the imaging device 2 in the imaging device bay 3 (hence optionally providing a video feed as described further herein).

The image acquisition device 2 can be a Magnetic Resonance (MR) image acquisition device, a Computed Tomography (CT) image acquisition device; a positron emission tomography (PET) image acquisition device; a single photon emission computed tomography (SPECT) image acquisition device; an X-ray image acquisition device; an ultrasound (US) image acquisition device; or a medical imaging device of another modality. The imaging device 2 may also be a hybrid imaging device such as a PET/CT or SPECT/CT imaging system. While a single image acquisition device 2 is shown by way of illustration in FIG. 1, more typically a medical imaging laboratory will have multiple image acquisition devices, which may be of the same and/or different imaging modalities. For example, if a hospital performs many CT imaging examinations and relatively fewer MRI examinations and still fewer PET examinations, then the hospital's imaging laboratory (sometimes called the "radiology lab" or some other similar nomenclature) may have three CT scanners, two MRI scanners, and only a single PET scanner. This is merely an example. Moreover, the remote service center 4 may provide service to multiple hospitals. The local operator controls the medical imaging device 2 via an imaging device controller 10. The remote operator is stationed at a remote workstation 12 (or, more generally, an electronic controller 12).

As used herein, the term "medical imaging device bay" (and variants thereof) refer to a room containing the medical imaging device 2 and also any adjacent control room containing the medical imaging device controller 10 for controlling the medical imaging device. For example, in reference to an MRI device, the medical imaging device bay 3 can include the radiofrequency (RF) shielded room containing the MRI device 2, as well as an adjacent control room housing the medical imaging device controller 10, as understood in the art of MRI devices and procedures. On the other hand, for other imaging modalities such as CT, the imaging device controller 10 may be located in the same room as the imaging device 2, so that there is no adjacent control room and the medical bay 3 is only the room containing the medical imaging device 2. In addition, while FIG. 1 shows a single medical imaging device bay 3, it will be appreciated that the remote service center 4 (and more particularly the remote workstation 12) is in communication with multiple medical bays via a communication link 14, which typically comprises the Internet augmented by local area networks at the remote expert RE and local operator LO ends for electronic data communications. In addition, while FIG. 1 shows a single remote service center 4, it will be appreciated that the remote service center is in communication with multiple medical bays 3 via the communication link 14.

As diagrammatically shown in FIG. 1, in some embodiments, a camera 16 (e.g., a video camera) is arranged to acquire a video stream or feed 17 of a portion of a workspace of the medical imaging device bay 3 that includes at least the area of the imaging device 2 (such as, for example, the medical imaging device controller 10) where the local operator LO interacts with the patient, and optionally may further include the imaging device controller 10. In other embodiments, a microphone 13 is arranged to acquire an audio stream or feed 18 of the workspace that includes audio noises occurring within the medical imaging device bay 3 (e.g., verbal instructions by the local operator LO, questions from the patient, and so forth). In further embodiments, software signals software signal streams or feeds 9 (e.g., data streams, screen-sharing streams from a scraped screen of the medical imaging device controller) from electronic medical devices 8, 10 disposed in the workspaces of the local operators LO are obtained. In one such example, one or more sensors 8 dispersed throughout the medical imaging bay 3 are configured to acquire event streams 9 related to events (e.g., movement by people, operations performed by the medical imaging device 2, patient and room preparation for the imaging examination, patient alerts, an indication of an opening of a door on the medical imaging device 2, an indication of commencement of an intravenous drip, an indication of an intercom being used, a respiration or cardiac senor output, and so forth). The video stream 17 and/or the audio stream 18 and/or the event streams 9 is sent to the remote workstation 12 via the communication link 14, e.g. as a streaming video feed received via a secure Internet link. To do so, the feeds 17, 18, 9 are collected with a feed aggregator 15 disposed in the medical imaging device bay 3, and transmitted via communication link 14.

The communication link 14 also provides a natural language communication pathway 19 for verbal and/or textual communication between the local operator and the remote operator. For example, the natural language communication link 19 may be a Voice-Over-Internet-Protocol (VOIP) telephonic connection, an online video chat link, a computerized instant messaging service, or so forth. Alternatively, the natural language communication pathway 19 may be provided by a dedicated communication link that is separate from the communication link 14 providing the data communications 17, 18, e.g. the natural language communication pathway 19 may be provided via a landline telephone. In some embodiments, the natural language communication link 19 allows a local operator LO to call a selected remote expert RE. The call, as used herein, can refer to an audio call (e.g., a telephone call), a video call (e.g., a Skype or Facetime or another screen-sharing program), or an audio-video call.

FIG. 1 also shows, in the remote service center 4 including the remote workstation 12, such as an electronic processing device, a workstation computer, or more generally a computer, which is operatively connected to receive and present the video feed 17 of the medical imaging device bay 3 from the camera 16 and/or to the audio feed 18, and/or the event data stream(s) 9. Additionally or alternatively, the remote workstation 12 can be embodied as a server computer or a plurality of server computers, e.g. interconnected to form a server cluster, cloud computing resource, or so forth. The workstation 12 includes typical components, such as an electronic processor 20 (e.g., a microprocessor), at least one user input device (e.g., a mouse, a keyboard, a trackball, and/or the like) 22, and at least one display device 24 (e.g. an LCD display, plasma display, cathode ray tube display, and/or so forth). In some embodiments, the display device 24 can be a separate component from the workstation 12. The display device 24 may also comprise two or more display devices, e.g. one display presenting the video feed 17 and the other display presenting the audio stream 18 and/or the event data stream 9. Alternatively, the video feed 17, the audio feed 18, and/or the event data feed 9 may be presented on a single display in respective windows. The electronic processor 20 is operatively connected with a one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the workstation 12, various combinations thereof, or so forth. It is to be understood that any reference to a non-transitory medium or media 26 herein is to be broadly construed as encompassing a single medium or multiple media of the same or different types. Likewise, the electronic processor 20 may be embodied as a single electronic processor or as two or more electronic processors. The non-transitory storage media 26 stores instructions executable by the at least one electronic processor 20. The instructions include instructions to generate a graphical user interface (GUI) 28 for display on the remote operator display device 24.

The medical imaging device controller 10 in the medical imaging device bay 3 also includes similar components as the remote workstation 12 disposed in the remote service center 4. Except as otherwise indicated herein, features of the medical imaging device controller 10, which includes a local workstation 12', disposed in the medical imaging device bay 3 similar to those of the remote workstation 12 disposed in the remote service center 4 have a common reference number followed by a "prime" symbol, and the description of the components of the medical imaging device controller 10 will not be repeated. In particular, the medical imaging device controller 10 is configured to display a GUI 28' on a display device or controller display 24' that presents information pertaining to the control of the medical imaging device 2, such as configuration displays for adjusting configuration settings an alert 30 perceptible at the remote location when the status information on the medical imaging examination satisfies an alert criterion of the imaging device 2, imaging acquisition monitoring information, presentation of acquired medical images, and so forth. The communication link 14 allows for screen sharing between the display device 24 in the remote service center 4 and the display device 24' in the medical imaging device bay 3. The GUI 28' includes one or more dialog screens, including, for example, an examination/scan selection dialog screen, a scan settings dialog screen, an acquisition monitoring dialog screen, among others. The GUI 28' can be included in the video feed 17 or the mirroring data stream 17' and displayed on the remote workstation display 24 at the remote location 4.

FIG. 1 shows an illustrative local operator LO, and an illustrative remote expert RE (i.e. expert, e.g. supertech). However, in a Radiology Operations Command Center (ROCC) as contemplated herein, the ROCC provides a staff of supertechs who are available to assist local operators LO at different hospitals, radiology labs, or the like. Each remote expert RE can operate a corresponding remote workstation 12. The ROCC may be housed in a single physical location, or may be geographically distributed. For example, in one contemplated implementation, the remote expert RE are recruited from across the United States and/or internationally in order to provide a staff of supertechs with a wide range of expertise in various imaging modalities and in various imaging procedures targeting various imaged anatomies. In view of this multiplicity of local operators LO and multiplicity of remote expert RE, the disclosed communication link 14 includes a server computer 32 (or a cluster of servers, cloud computing resource comprising servers, or so forth) which is programmed to establish connections between selected local operator LO/remote expert RE pairs. For example, if the server computer 32 is Internet-based, then connecting a specific selected local operator LO/remote expert RE connection can be done using Internet Protocol (IP) addresses of the various components 16, 10, 12, the telephonic or video terminals of the natural language communication pathway 19, et cetera. The server computer 32 is operatively connected with a one or more non-transitory storage media or data storage 34. The non-transitory storage media 34 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the server computer 32, various combinations thereof, or so forth. It is to be understood that any reference to a non-transitory medium or media 34 herein is to be broadly construed as encompassing a single medium or multiple media of the same or different types. Likewise, the server computer 32 may be embodied as a single electronic processor or as two or more electronic processors. The non-transitory storage media 34 stores instructions executable by the server computer 32. In addition, the non-transitory computer readable medium 34 (or another database) stores data related to a set of remote experts RE and/or a set of local operators LO. The remote expert data can include, for example, skill set data, work experience data, data related to the difficulty of the examination, data related to ability to work on multi-vendor modalities, data related to experience with the local operator LO and so forth.

The non-transitory storage media 34 of the server computer 32 is configured to store a plurality of view configurations 36 for a plurality of views displayed via the GUI 28 on the display device 24 of the remote workstations 12 operable by individual remote experts RE. The view configurations 36 can include, for example, an imaging bay UI view configuration for presenting information including at least the imaging bay video feed 17 of a selected local operator LO, and a controller display UI view configuration for presenting information including at least the controller display feed of a selected local operator. A view configuration may include, by way of non-limiting example: one or more windows shown on the display device 24 such as a window presenting video acquired by a camera 16, a window presenting a shared screen of the medical imaging device controller 10, or so forth; an information display window or screen section presenting textual information such as identifiers of the imaging location or so forth, status of an imaging examination, and et cetera; a graphical display presenting information in a bar graph, trendline, or so forth; a display window for presenting an acquired medical image; an audio feed from a microphone 13 or from the mic of the video camera 16; various combinations thereof; and so forth. When the local operator LO calls a select remote expert RE, then the corresponding view configuration(s) 36 for the called remote expert can be retrieved from the non-transitory computer readable medium 34 of the server computer 32 and displayed on the remote workstation 12 of the remote expert RE who was called.

In addition, the non-transitory storage media 34 of the server computer 32 is configured to store (i) an event prioritization mapping process 38 that maps events detected in the feeds 17, 18, 9 to priority levels and an event-to-view mapping, and (ii) an event-to-view mapping 40 that maps events to UI views. In some embodiments, the processes 38, 40 can be implemented using look-up tables. In other embodiments, the event-to-view mapping process 38 is configured to map events occurring in the imaging bay 3 to the imaging bay UI view, and maps events relating to the medical imaging device 2 to the controller display UI view. For example, the event-to-view mapping 40 can include associations of the events to the corresponding UI view. These associations can include, for example, patient problem on-site event (e.g., the patient is moving inside a bore of the medical imaging device 2) is associated with a view of the patient or the bore; an intravenous drop injection commencement event is associated with a view of the controller screen of the intravenous device; an image acquisition/ending event is associated with a view of the acquired images, and so forth. These are merely non-limiting examples, and should not be construed as limiting.

Furthermore, as disclosed herein, the server computer 32 performs a method or process 100 supporting a remote expert RE in assisting local operators LO of respective medical imaging devices 2 during medical imaging examinations. It will be appreciated that the method 100 can also be suitably performed by one of the remote workstations 12.

Figure 2:
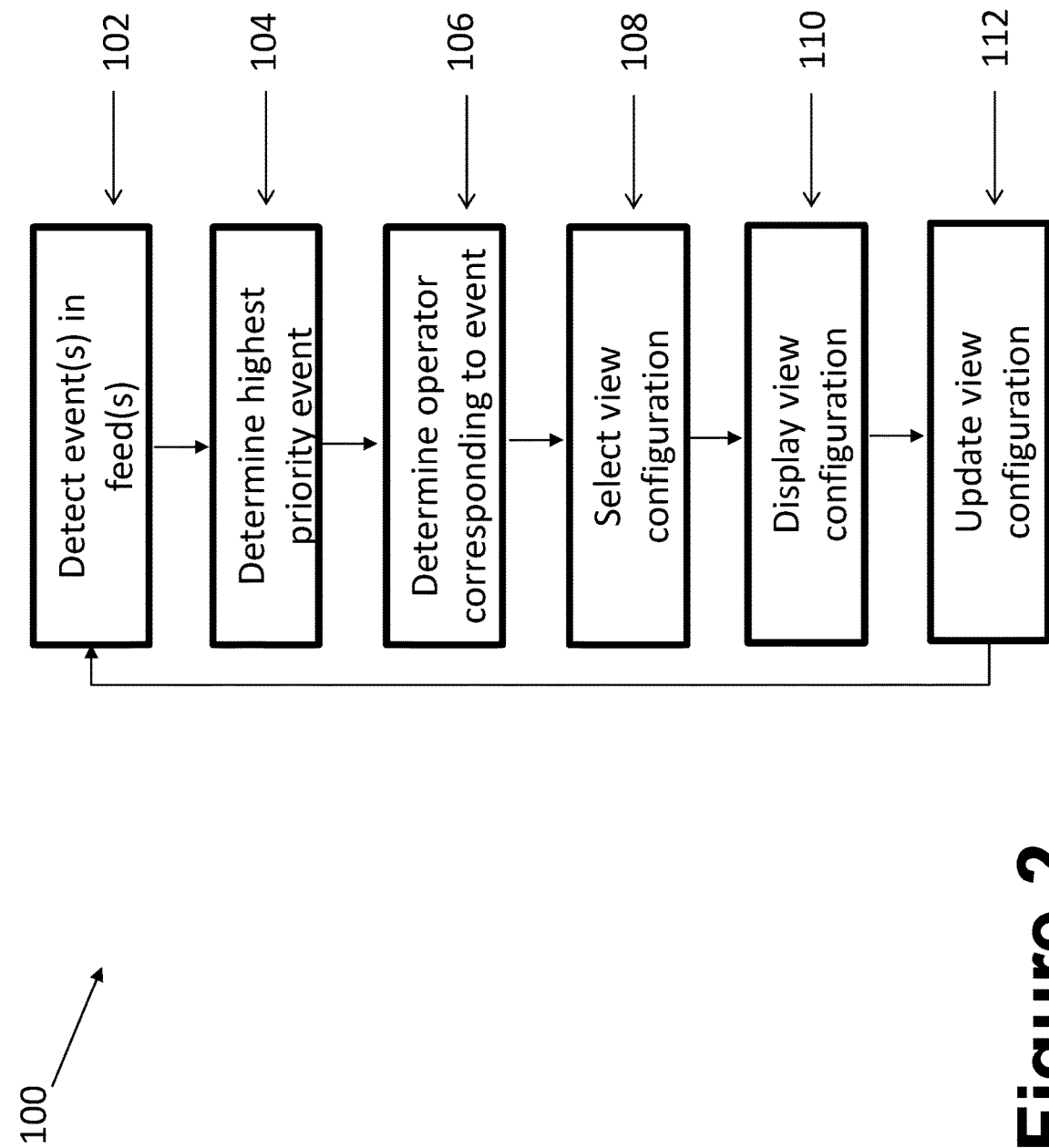
FIG. 2 shows an example flow chart of operations suitably performed by the apparatus of FIG. 1.

With reference to FIG. 2, and with continuing reference to FIG. 1, an illustrative embodiment of method 100 supporting a remote expert RE in assisting local operators LO of respective medical imaging devices 2 during medical imaging examinations performed by the server computer 32 is diagrammatically shown as a flowchart. To begin the method 100, an imaging examination is commended by the local operator LO using the medical imaging device 2. An event can occur during the examination which requires assistance from a remote expert RE. The feed aggregator 15 is then configured to collect and route the video feed 17 (acquired by the one or more cameras 16 and/or the audio feed 18 (acquired by the one or more microphones 13) and/or the event feed 9 (acquired by the one or more sensors 8) to the workstations 12 of respective remote experts and the server computer 32, and to route audio/video calls via the natural language communication pathway 19, from local operators LO to the workstations of the respective remote experts.

At an operation 102, the signal feeds 17, 18, 9 are analyzed to detect events occurring in the workspaces of the local operators. At an operation 104, a highest priority event from amongst the detected events is identified using the event prioritization mapping process (e.g., lookup table) 38. At an operation 106, a highest priority local operator LO is identified as the local operator in whose workspace the highest priority event occurred. At an operation 108, a highest priority UI view (e.g., a corresponding view configuration 36) corresponding to the highest priority event is selected using the event-to-UI view mapping process (e.g., look-up table) 40. At an operation 110, information derived from the signal feeds 17, 18, 9 are presented on the remote workstation 12 in accordance with the highest priority UI view (i.e., the view configuration 36). From here, the remote expert RE can assist the local operator LO with the detected event for that local operator (e.g., the highest priority event). Once this event is resolved, the remote expert RE can indicate (e.g., via the at least one user input device 22) that the event is resolved, and can be removed from a queue of events. At an operation 112, the GUI 28 of the remote workstation 12 can be switched or updated to another event by repeating the operations 102-110.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A system for supporting a remote expert (RE) in assisting local operators (LO) of respective medical imaging devices during medical imaging examinations, the system comprising:
a feed aggregator operatively connected to receive signal feeds from electronic devices disposed in workspaces of the local operators;
a remote workstation providing a user interface (UI) with selectable UI views for presenting information derived from the signal feeds from the workspace of a selected local operator in accordance with a selected UI view, the workstation including at least one display device and at least one user input device;
a non-transitory data storage that stores an event prioritization mapping that maps events to priority levels and an event-to-view mapping that maps events to UI views; and
an electronic processor programmed to:
analyze the signal feeds received by the feed aggregator to detect events occurring in the workspaces of the local operators;
identify a highest priority event from amongst the detected events using the event prioritization mapping;
identify a highest priority local operator as the local operator in whose workspace the highest priority event occurred;
select a highest priority UI view corresponding to the highest priority event using the event-to-UI view mapping; and
present information derived from the signal feeds from the workspace of the highest priority local operator in accordance with the highest priority UI view.

2. The system of claim 1, wherein the signal feeds received by the feed aggregator include:
video feeds acquired by cameras disposed in the workspaces of the local operators (LO), and
software signal feeds from electronic medical devices disposed in the workspaces of the local operators including at least imaging device controllers of the respective medical imaging devices operated by the respective local operators.

3. The system of claim 1, wherein:
the signal feeds received by the feed aggregator include imaging bay video feeds acquired by cameras disposed in the imaging bays of the local operators (LO), and controller display feeds of controllers of the medical imaging devices operated by the local operators;

the UI views include at least an imaging bay UI view for presenting information including at least the imaging bay video feed of a selected local operator, and a controller display UI view for presenting information including at least the controller display feed of a selected local operator; and
the event-to-view mapping maps events occurring in the imaging bay to the imaging bay UI view and maps events relating to the medical imaging device to the controller display UI view.

4. The system of claim 1, wherein the signal feeds received by the feed aggregator include:
sensor signals from event sensors disposed in the workspaces of the local operators.

5. The system of claim 1, wherein the electronic processor is further programmed to:
in response to receiving an indication that the highest priority event has been resolved via the at least one user input device of the remote workstation, switching the UI to another event by repeating: the analysis to detect events, the identification of the highest priority event, the identification of the highest priority UI view, and the presenting of information.

6. The system of claim 1, wherein the event prioritization mapping includes:
inputting the signal feed into a look-up table that associates a priority level to the events in the signal feeds.

7. The system of claim 1, wherein the event-to-UI view mapping includes:
inputting the identified highest priority event into a look-up table to select the highest priority UI view.

8. A non-transitory computer readable medium storing instructions executable by at least one electronic processor to perform a method of controlling a user interface (UI) provided by a remote operator workstation of a remote expert (RE) providing assistance to local operators (LO) of respective medical imaging devices during a medical imaging examination, the method comprising:
analyzing signal feeds received from workspaces of the local operators to detect events occurring in the workspaces of the local operators;
identifying a highest priority event from amongst the detected events using an event prioritization mapping;
identifying a highest priority local operator as the local operator in whose workspace the highest priority event occurred;
selecting a highest priority UI view corresponding to the highest priority event using an event-to-UI view mapping; and
presenting information derived from the signal feeds from the workspace of the highest priority local operator in accordance with the highest priority UI view.

9. The non-transitory storage medium of claim 8, wherein the received signal feeds include:
video feeds acquired by cameras disposed in the workspaces of the local operators (LO), and
software signal feeds from electronic medical devices disposed in the workspaces of the local operators including at least imaging device controllers of the respective medical imaging devices operated by the respective local operators.

10. The non-transitory storage medium of claim 8, wherein:
the signal feeds received by the feed aggregator include imaging bay video feeds acquired by cameras disposed in the imaging bays of the local operators (LO), and controller display feeds of controllers of the medical imaging devices operated by the local operators;

the UI views include at least an imaging bay UI view for presenting information including at least the imaging bay video feed of a selected local operator, and a controller display UI view for presenting information including at least the controller display feed of a selected local operator; and the event-to-view mapping maps events occurring in the imaging bay to the imaging bay UI view and maps events relating to the medical imaging device to the controller display UI view.

11. The non-transitory storage medium of claim 9, wherein the signal feeds received by the feed aggregator include:

sensor signals from event sensors disposed in the workspaces of the local operators; and software signals generated by software running on the controllers of the medical imaging devices and/or by software running on medical devices in the workspaces of the local operators.

12. The non-transitory storage medium of claim 9, wherein the method further includes:

in response to receiving an indication that the highest priority event has been resolved via the at least one user input device of the remote workstation, switching the UI to another event by repeating: the analysis to detect events, the identification of the highest priority event, the identification of the highest priority UI view, and the presenting of information.

13. The non-transitory storage medium of claim 9, wherein the event prioritization mapping includes:

inputting the signal feed into a look-up table that associates a priority level to the events in the signal feeds.

14. The non-transitory storage medium of claim 9, wherein the event-to-UI view mapping includes:

inputting the identified highest priority event into a look-up table to select the highest priority UI view.

15. A method of controlling a user interface (UI) provided by a remote operator workstation of a remote expert (RE) providing assistance to local operators (LO) of respective medical imaging devices during a medical imaging examination, the method comprising:

analyzing signal feeds received from workspaces of the local operators to detect events occurring in the workspaces of the local operators;

identifying a highest priority event from amongst the detected events using an event prioritization mapping by inputting the signal feeds into a look-up table that associates a priority level to the events in the signal feeds;

identifying a highest priority local operator as the local operator in whose workspace the highest priority event occurred;

selecting a highest priority UI view corresponding to the highest priority event using an event-to-UI view mapping by inputting the identified highest priority event into a look-up table to select the highest priority UI view; and presenting information derived from the signal feeds from the workspace of the highest priority local operator in accordance with the highest priority UI view.

16. The method of claim 15, wherein the received signal feeds include:

video feeds acquired by cameras disposed in the workspaces of the local operators (LO), and software signal feeds from electronic medical devices disposed in the workspaces of the local operators including at least imaging device controllers of the respective medical imaging devices operated by the respective local operators.

17. The method of claim 15, wherein:

the signal feeds received by the feed aggregator include imaging bay video feeds acquired by cameras disposed in the imaging bays of the local operators (LO), and controller display feeds of controllers of the medical imaging devices operated by the local operators;

the UI views include at least an imaging bay UI view for presenting information including at least the imaging bay video feed of a selected local operator, and a controller display UI view for presenting information including at least the controller display feed of a selected local operator; and the event-to-view mapping maps events occurring in the imaging bay to the imaging bay UI view and maps events relating to the medical imaging device to the controller display UI view.

18. The method of claim 15, wherein the signal feeds received by the feed aggregator include:

sensor signals from event sensors disposed in the workspaces of the local operators; and software signals generated by software running on the controllers of the medical imaging devices and/or by software running on medical devices in the workspaces of the local operators.

19. The method of claim 15, further including:

in response to receiving an indication that the highest priority event has been resolved via the at least one user input device of the remote workstation, switching the UI to another event by repeating: the analysis to detect events, the identification of the highest priority event, the identification of the highest priority UI view, and the presenting of information.

20. The method of claim 15, wherein the event prioritization mapping includes:

inputting the signal feed into a look-up table that associates a priority level to the events in the signal feeds.

* * * * *